United States Patent
Zhang et al.

(10) Patent No.: US 7,595,491 B2
(45) Date of Patent: Sep. 29, 2009

(54) METHODS AND SYSTEMS FOR THE ENHANCEMENT OF TERAHERTZ WAVE GENERATION FOR ANALYZING A REMOTELY-LOCATED OBJECT

(75) Inventors: Xi-Cheng Zhang, Melrose, NY (US); Jianming Dai, Troy, NY (US); Xu Xie, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 216 days.

(21) Appl. No.: 11/756,230

(22) Filed: May 31, 2007

(65) Prior Publication Data

US 2007/0263682 A1 Nov. 15, 2007

Related U.S. Application Data

(63) Continuation-in-part of application No. 11/610,824, filed on Dec. 14, 2006.

(60) Provisional application No. 60/868,140, filed on Dec. 1, 2006, provisional application No. 60/754,096, filed on Dec. 27, 2005.

(51) Int. Cl.
G01N 21/17 (2006.01)

(52) U.S. Cl. .................................. 250/341.1

(58) Field of Classification Search ............ 250/341.1
See application file for complete search history.

(56) References Cited

U.S. PATENT DOCUMENTS

| | | | |
|---|---|---|---|
| 5,939,721 A | 8/1999 | Jacobsen et al. | 250/330 |
| 6,111,416 A | 8/2000 | Zhang et al. | 324/753 |
| 6,977,379 B2 | 12/2005 | Zhang et al. | 250/341.1 |
| 2005/0242287 A1 | 11/2005 | Hakimi | 250/363.09 |
| 2005/0282407 A1* | 12/2005 | Bruland et al. | 438/795 |

FOREIGN PATENT DOCUMENTS

| | | |
|---|---|---|
| GB | 2396695 | 6/2004 |
| GB | 2399626 | 9/2004 |
| WO | WO 00/75641 | 12/2000 |

OTHER PUBLICATIONS

Zhang et al., International Search Report, PCT Patent Application No. PCT/US2006/062091 (5 pages), entitled "Method of Analyzing A Remotely Located Object Utilizing An Optical Technique to Detect Terahertz Radiation," filed Dec. 14, 2006 (5 pages).

(Continued)

*Primary Examiner*—Constantine Hannaher
(74) *Attorney, Agent, or Firm*—Heslin Rothenberg Farley & Mesiti P.C.

(57) ABSTRACT

A method for generating terahertz radiation includes inducing a background plasma in a volume of a gas by focusing a first optical beam in the volume, and generating pulsed terahertz radiation with enhanced generation efficiency by focusing a second time-delayed optical beam in the background plasma. The method may be implemented in a system for detecting and analyzing a remotely-located object.

43 Claims, 10 Drawing Sheets

OTHER PUBLICATIONS

Federicli, John F. et al., "THz Standoff Detection and Imaging of Explosives and Weapons," Optics and Photonics in Global Homeland Security, Proc. SPIE, vol. 5781, pp. 75-84 (2005).

G. Méchain, A. Mysyrowicz, M. Depiesse, M. Pellett, "A Virtual Antenna Produced In Air By Intense Femtosecond Laser Pulses," (Nov. 3, 2005), Proc. SPIE, vol. 5989, 59890S (2005) DOI; 10.1117/12.631202(6 Pages).

Zandonella, Catherine, "T-Ray Specs," Nature, vol. 424, pp. 721-722, Aug. 14, 2003.

Bartel et al., "Generation of Single-Cycle THZ Transients with High Electric-Field Amplitudes," Optics Letters, vol. 30, No. 20, 3-pages, Oct. 15, 2005.

Cook et al., "Intense Terahertz Pulses by Four-Wave Rectification in Air," Optics Letters, vol. 25, No. 16, pp. 1210-1212, Aug. 15, 2000.

Dai et al., "Detection of Broadband Terahertz Waves with a Laser-Induced Plasma in Gases," Physical Review Letters, Sep. 8, 2006, 4-pages.

Ferguson et al., "Materials for Terahertz Science and Technology," Nature Materials, vol. 1, pp. 26-33, Sep. 2002.

Hamster et al., "Short-Pulse Terahertz Radiation from high-Intensity-Laser-Produced Plasmas," Physical Review, vol. 49, No. 1, pp. 671-677, Jan. 1994.

Janke et al., "Inversionless Amplification of Coherent Terahertz Radiation," Physical Review Letters, vol. 67, pp. 155206-1 to 155206-4.

Kress et al., "Determination of the Carrier-Envelope Phase of Few-Cycle Laser Pulses with Terahertz-Emission Spectroscopy," Nature Physics, vol. 2, pp. 327-331, May 2006.

Kress et al., "Terahertz-Pulse Generation by Photoionization of Air with Laser Pulses Composed of Both Fundamental and Second-Harmonic Waves," Optics Letters, vol. 29, No. 10, pp. 1120-1122, May 15, 2004.

Löffler et al., "Efficient Terahertz Pulse Generation in Laser-Induced Gas Plasmas," Acta Physica Polonica A, vol. 107, No. 1, pp. 99-108, 2005.

Martini et al., "Inversionless Amplification of Coherent THz Radiation," IEEE, pp. 242-245, 1998. THz 98, IEEE 6th Intl Conf on THz Electronics, Sep. 3-4, 1998.

Meyer et al., "Phase-Matched High-Order Difference-Frequency Mixing in Plasmas," Physical Review Letters, vol. 26, No. 18, pp. 3336-3339, Apr. 29, 1996.

Théberge et al., "Tunable Ultrashort Laser Pulses Generated Through Filamentation in Gases," Physical Review Letters, vol. 97, pp. 023904-1 to 023904-5, Jul. 14, 2006.

Tzortzakis et al., "Coherent Subterahertz Radiation from Femtosecond Infrared Filaments in Air," Optics Letters, vol. 27, No. 21, pp. 1944-1946, Nov. 1, 2002.

Van Exter et al., "High-Brightness Terahertz Beams Characterized with an Ultrafast Detector," Applied Physics Letters, vol. 55, No. 4, pp. 337-339, Jul. 24, 1989.

Wu et al., "Broadband Detection Capability of ZnTe Electro-Optic Field Detectors," Applied Physics Letters, vol. 68, No. 21, pp. 2924-2926, May 20, 1996.

Xie et al, "Coherent Control of THz Wave Generation in Ambient Air," Physical Review Letters, vol. 96, pp. 075005-1 to 075005-4, Feb. 24, 2006.

Xie et al., "Enhancement of Terahertz Wave Generation from Laser Induced Plasma," Applied Physics Letters, vol. 90, 2007, 141104, 3-pages, Apr. 4, 2007.

Zhang et al., pending U.S. Utility Appl. No. 11/610,824, filed Dec. 14, 2006 entitled "Method of Analyzing a Remotely-Located Object Utilizing an Optical Technique to Detect Terahertz Radiation".

Zhang et al., pending U.S. Utility Appl. No. 11/756,243, filed May 31, 2007 entiled "Methods and Systems for Generating Amplified Terahertz Radiation for Analyzing Remotely-Located Objects".

Zhu et al., "Long Lifetime Plasma Channel in Air Generated by Multiple Femtosecond Laser Pulses and an External Electrical Field," Optics Express, vol. 14, No. 11, pp. 4915-4922, May 29, 2006.

Agrawal, Govind P., "Nonlinear Fiber Optics," Third Edition, Academic Press, San Diego, 1-page, 2001, cover only.

Reimann, et al., "Direct Field-Resolved Detection of Terahertz Transients with Amplitudes of Megavolts per Centimeter," Optics Letters, vol. 28, No. 6, pp. 471-473, Mar. 15, 2003.

Carr et al., "High-Power Terahertz Radiation From Relativistic Electrons," Nature, vol. 420, pp. 153-156, Nov. 2002.

Chin et al., "The Propagation of Powerful Femtosecond Laser Pulses in Optical Media: Physics, Application, and New Challenges [1,2]," Canadian Journal of Physics, vol. 83, No. 9, pp. 863-905, Sep. 2005.

Cole et al., "Coherent Manipulation of Semiconductor Quantum Bits with Terahertz Radiation," Nature, vol. 410, pp. 60-63, Mar. 2001.

Cook et al., "Terahertz-Field-Induced Second-Harmonic Generation Measurements of Liquid Dynamics," Chemical Physics Letters, vol. 309, pp. 221-228, Aug. 13, 1999.

Grischkowsky et al., Far-infrared Time-Domain Spectroscopy with Terahertz Beams of Dielectrics and Semiconductors, J. Optical Society America B, vol. 7, No. 10, pp. 2006-2015, Oct. 1990.

Huber et al., "How Many-Particle Interactions Develop After Ultra Fast Excitation of an Electron-Hole Plasma," Nature, vol. 414, pp. 286-289, Nov. 2001.

Kaindl et al., "Ultrafast terahertz Probes of Transient Conducting and Insulation Phases in an Electron-Hole Gas," Nature, vol. 423, pp. 734-738, Jun. 12, 2003.

Köhler et al., "Terahertz Semiconductor-Heterostructure Laser," Nature, vol. 417, pp. 156-159, May 9, 2002.

Nahata et al., "Detection of Freely Propagating Terahertz Radiation by Use of Optical Second-Harmonic Generation," Optics Letters, vol. 23, No. 1, pp. 67-69, Jan. 1, 1998.

Wang et al., "Metal Wires for Terahertz Wave Guiding," Nature, vol. 432, pp. 376-379, Nov. 18, 2004.

Wu et al., "Free-Space Electro-Optic Sampling of Terahertz Beams," American Physics Letters, vol. 67, No. 24, pp. 32523-33525, Dec. 11, 1995.

Zhong et al., "Terahertz Emission Profile From Laser-Induced Air Plasma," Applied Physics Letters, vol. 88, pp. 261103-1-261103-3, 2006.

Hamster et al., "Subpicosecond, Electromagnetic Pulses from Intense Laser-Plasma Interaction," Physical Review Letters, vol. 71, No. 17, pp. 2725-2728, Oct. 25, 1993.

Walsh et al., "The Tunnel Ionization of Atoms, Diatomic and Triatomic Molecules Using Intense 10.6 µm Radiation," Phys. B: At. Mol. Opt. Phys. vol. 27, pp. 3767-3779, 1994.

A. Couairon et al., "Propagation of twin laser pulses in air and concatenation of plasma strings produced by femtosecond infrared filaments." Optics Communications 225 (2003) 177-192. DOI: 10.1016/j.optcom.2003.07.11, 2003, 32-pages.

T.R. Nelson et al., "Laser filamentation of a femtosecond pulse in air at 400nm." QELS '01 Technical Digest, Summaries of Papers Presented at the Quantum Electronics and Laser Science Conference, 2001 261-262. DOI: 10.1109/QELS.2001.962222.

\* cited by examiner

METHODS AND SYSTEMS FOR THE ENHANCEMENT OF TERAHERTZ WAVE GENERATION FOR ANALYZING A REMOTELY-LOCATED OBJECT

CLAIM TO PRIORITY AND CROSS-REFERENCE TO RELATED APPLICATIONS

This application claims priority under 35 U.S.C. §119 to U.S. Provisional Application No. 60/868,140, filed Dec. 1, 2006, entitled "Enhancement of THz Wave Generation From Laser Induced Plasma", which is herein incorporated by reference in its entirety.

This application is also a continuation-in-part application of commonly owned pending U.S. patent application Ser. No. 11/610,824 filed Dec. 14, 2006, entitled "Method of Analyzing A Remotely-Located Object Utilizing An Optical Technique To Detect Terahertz Radiation" which claims priority under 35 U.S.C. §119 to U.S. Provisional Application No. 60/754,096, filed Dec. 27, 2005, the entire subject matter of these applications are incorporated herein by reference.

GOVERNMENT RIGHTS STATEMENT

This invention was made with U.S. Government support under Grant No. ECS-0621522 from the National Science Foundation and Grant No. DAAD 19-02-1-0255 from the Army Research Office. The U.S. Government has certain rights in the invention.

This application is related to commonly owned and concurrently filed U.S. patent application Ser. No. 11/756,243, entitled "Methods And Systems For Generating Amplified Terahertz Radiation For Analyzing Remotely-Located Objects", which claims priority under 35 U.S.C. §119 to U.S. Provisional Application No. 60/868,148, filed Dec. 1, 2006, entitled "THz Wave Amplification In Laser-Induced air Plasma", the entire subject matter of these applications are incorporated herein by reference.

FIELD OF THE INVENTION

The present invention generally relates to generating and detecting terahertz radiation. More particularly, the present invention relates to utilizing optical-wavelength radiation to facilitate remote analysis of an object with terahertz radiation.

BACKGROUND OF THE INVENTION

Improvised explosive devices (IEDs) are extremely dangerous partially because they are difficult to identify. A device capable of remote and in situ monitoring to detect concealed explosives would be very beneficial for a number of defense and homeland security uses.

Since terahertz wave spectroscopy has been utilized to detect a number of chemical and explosive materials and related compounds by providing their spectral signatures in the terahertz frequency range, it may have use in defense and security applications. For example, there is interest in terahertz wave spectroscopy as a technique to sense improvised explosive devices (IEDs). However, due to severe water vapor attenuation of terahertz waves in the atmosphere, reliable sensing range of terahertz wave spectroscopy has been limited to relatively short distances. For example, even though propagation of a pulsed terahertz wave for more than 145 meters has been achieved, spectroscopic measurement with an acceptable signal-to-noise ratio and false alarm rate is limited to about 30 meters. For defense and security applications, it is desirable to increase the reliable sensing range of terahertz wave spectroscopy.

Martini et al., in "Inversionless Amplification of Coherent THz Radiation", 1998 IEEE Sixth International Conference on Terahertz Electronics Proceedings, pages 242-245, (1998), described the utilization of the coherent nature of terahertz waves generated from a photoconductive antenna and has succeeded in building a terahertz cavity. In this design, superposition of a coherent terahertz wave and a coherent background can make fields add up before dephasing between these two waves sets in. By adding the background field, an enhancement (over 100%) based on coherent construction of the terahertz wave is realized. While enhancing the generation of terahertz waves, the enhanced terahertz waves are still subject to attenuation in the atmosphere due to water vapor as described above.

There is a need for further techniques for increasing the generation of terahertz waves and for increasing the range at which terahertz waves may be reliably sensed under a range of atmospheric conditions

SUMMARY OF THE INVENTION

The present invention provides, in a first aspect, a method for enhancing terahertz wave generation. The method includes providing a background plasma by directing a first optical beam in a volume of a gas, and enhancing pulsed terahertz wave generation by directing a second time-delayed optical beam in the background plasma.

The present invention provides, in a second aspect, a system for enhancing terahertz wave generation. The system includes a source for a first optical beam, means for directing the first optical beam to produce a background plasma in a volume of a gas, a source for a second time-delayed optical beam, and means for directing the second time-delayed optical beam in the background plasma to enhance pulsed terahertz wave generation.

The present invention provides, in a third aspect, a method for detecting a remotely-located object. The method includes providing a background plasma by directing an optical control beam in a volume of a gas, enhancing pulsed terahertz wave generation by directing a second time-delayed optical beam in the background plasma, providing a sensor plasma by directing an optical probe beam in another volume of the gas, and detecting an optical component of resultant radiation produced from an interaction of the optical probe beam and an incident terahertz wave in the sensor plasma, the incident terahertz wave being produced by an interaction of the enhanced pulsed terahertz wave with the targeted object.

The present invention provides, in a fourth aspect, a system for detecting a remotely-located object. The system includes a source for an optical control beam, means for directing the optical control beam to produce a background plasma in a volume of a gas, a source for a time-delayed optical signal beam, means for directing the time-delayed optical signal beam in the background plasma to enhance pulsed terahertz wave generation directed towards the targeted object, a source of an optical probe beam, means for directing the optical probe beam to produce a sensor plasma in another volume of the gas, and an optical detector for detecting an optical component of resultant radiation emitted from the sensor plasma as a result of an interaction, in the sensor plasma, of the optical probe beam and a resultant terahertz wave, the resultant terahertz wave comprising terahertz radiation reflected, scattered, or transmitted by the targeted object in response to an interaction of the enhanced pulsed terahertz radiation with the targeted object.

BRIEF DESCRIPTION OF THE DRAWINGS

The present matter which is regarded as the invention is particularly pointed out and distinctly claimed in the concluding portion of the specification. The present invention, however, may best be understood by reference to the following detailed description of various embodiments and the accompanying drawings in which:

DETAILED DESCRIPTION OF THE INVENTION

Figure 1:
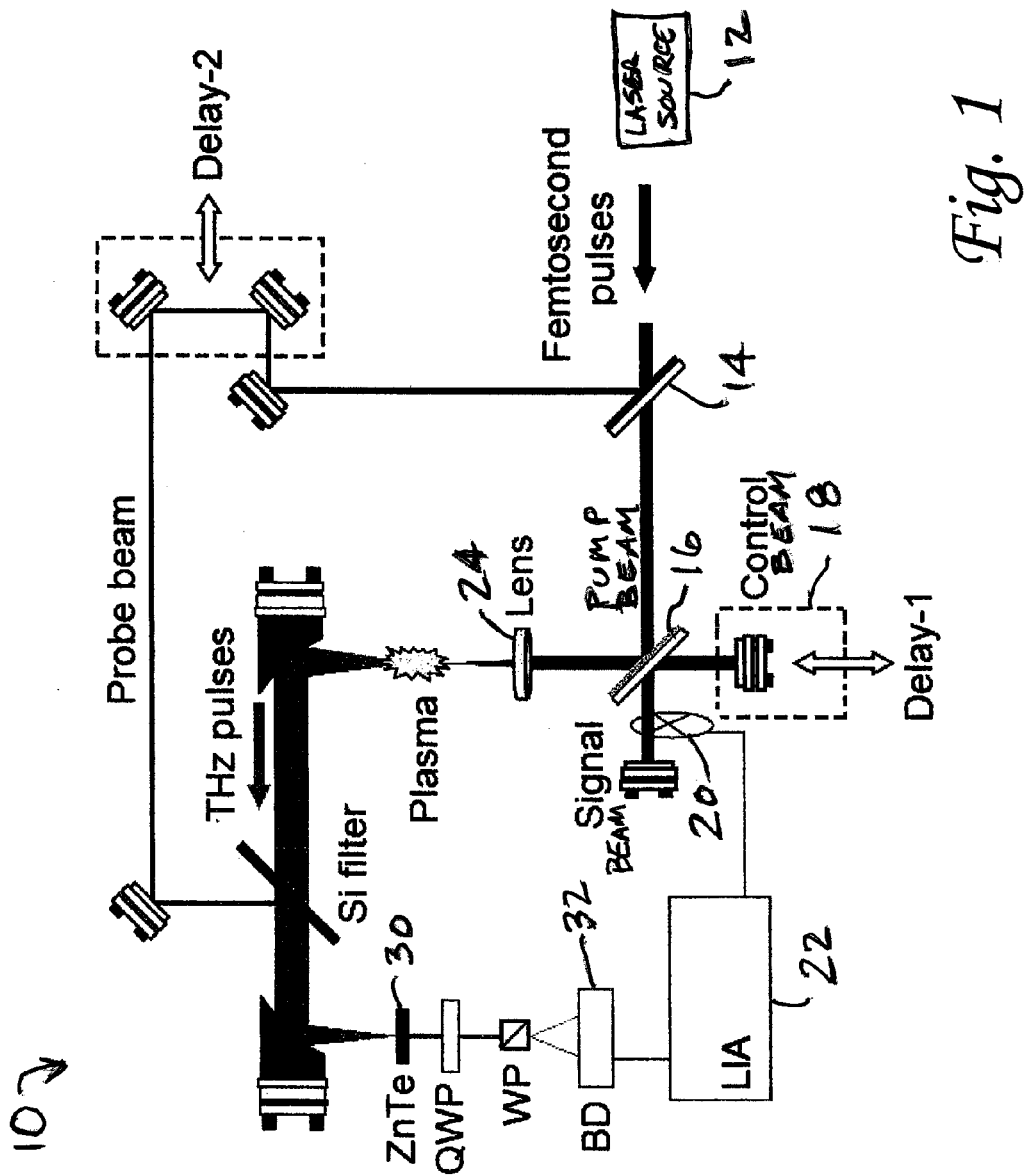
FIG. 1 is the schematic illustration of an experimental setup in accordance with the present invention for generating terahertz radiation with an enhanced generation efficiency in which an optical beam from a laser source is split into three beams, for example, an optical control beam, an optical signal beam, and an optical probe beam.

Pulsed terahertz wave spectroscopy is capable of sensing at short ranges compounds from which improvised explosive devices (IEDs) may be made. For example, the compound RDX has been detected at distances up to 30 meters in good weather, but the detection range using terahertz radiation may decrease to less than 10 meters in humid conditions. The reason is that the propagation of a terahertz wave in air is largely limited by water vapor absorption. For example, the attenuation of terahertz waves through the atmosphere is greater than 100 dB/km, even when the humidity level is only 20% at room temperature. Measurements of the attenuation effect at humidity levels from 3% to 100% indicate that, in ambient air, it may not be practical to get useful terahertz spectroscopy information from a terahertz wave traveling more than 100 meters. On the other hand, optical pulses (i.e. pulses of visible light, for example) have a significantly lower attenuation (on the order of 0.01 dB/km) than terahertz waves in the air.

Because optical pulses may be used to induce the generation of terahertz waves and to sense the incidence of the terahertz waves, optical radiation may be used advantageously in terahertz spectroscopy for remote generation and detection of terahertz waves to solve the problem of high attenuation of terahertz radiation in the atmosphere and thereby increase the effective range at which terahertz spectroscopy can detect explosive materials.

In one aspect, the present invention provides a technique for enhancing the generation of terahertz waves from a laser-induced plasma with a pre-existing background plasma. By using an optical laser pulse to pre-ionize air, for example at the same focal spot, an enhanced terahertz wave may be generated by a second temporally separated optical laser pulse. An enhancement up to 250% has been observed by the inventors with the use of ionized-air (air plasma) background, and the enhancement phenomenon lasts hundreds of picoseconds after the pre-ionized background is created.

In another aspect, the present invention provides a technique that utilizes the enhanced terahertz radiation to detect a remotely-located object such as explosives and explosive related compounds from a distance. As described in greater detail below, a plurality of temporally separated pulsed optical beams may be focused to ionize a volume of ambient gas close to the targeted object and generate a terahertz wave emitter plasma with enhanced terahertz generation efficiency. Another optical beam may be focused to ionize a volume of ambient gas to produce a terahertz wave sensor plasma. The sensor plasma may detect an incident terahertz wave that results from the enhanced terahertz radiation's interaction with the target. Interaction of the enhanced terahertz radiation with the target includes reflection, scattering, and transmission of the enhanced terahertz radiation by the target. An explosive or related compound may be detected by identifying the specified spectral fingerprint of the material in the terahertz wave detected by the sensor plasma.

Initially, with reference to FIG. 1, therein illustrated is an experimental setup 10 which demonstrates the enhancement of the terahertz wave generation with pre-created laser plasma in accordance with the present invention.

Laser pulses from a laser source 12 such as a Ti: sapphire amplifier (Spectra-Physics Hurricane i with 120 fs pulse duration, 800 µJ pulse energy and 1 kHz repetition rate) are split by a beam splitter 14 into an optical probe beam and an optical pump beam. The optical pump beam is also split by a beam splitter 16 such as a 50/50 beam splitter to form a Michelson interferometer. One beam is an optical control beam, and the other beam is an optical signal beam. The time delay between the optical control beam and optical signal beam is scanned by a temporal delay stage 18 (Delay-1), and a mechanical chopper 20 connected with a lock-in amplifier 22 is placed in the optical signal beam path. The optical control beam and optical signal beam are focused at the same point by a 2.5" focal length convex lens 24. The average powers of optical control beam and the optical signal beam at the focal spot are both about 160 mW (160 µJ pulse energy).

In the experiment, a temporal delay between the optical control beam and the optical signal beam (Delay-1) was adjusted. At each specific delay of the Delay-1, the optical probe beam is scanned (Delay-2) to obtain the terahertz temporal waveform. The terahertz radiation was measured by using a nonlinear optical crystal 30 such as a 3 mm thick <110> oriented ZnTe crystal through electric optical sampling. Lock-in amplifier 22 analyzes the data from a balanced detector pair 32. A four-wave-mixing method with the optical signal beam was not used to generate the terahertz wave in order to avoid the optical interference in a BBO crystal. Therefore, only an 800 nm laser beam was used in the experiment.

Figure 2:
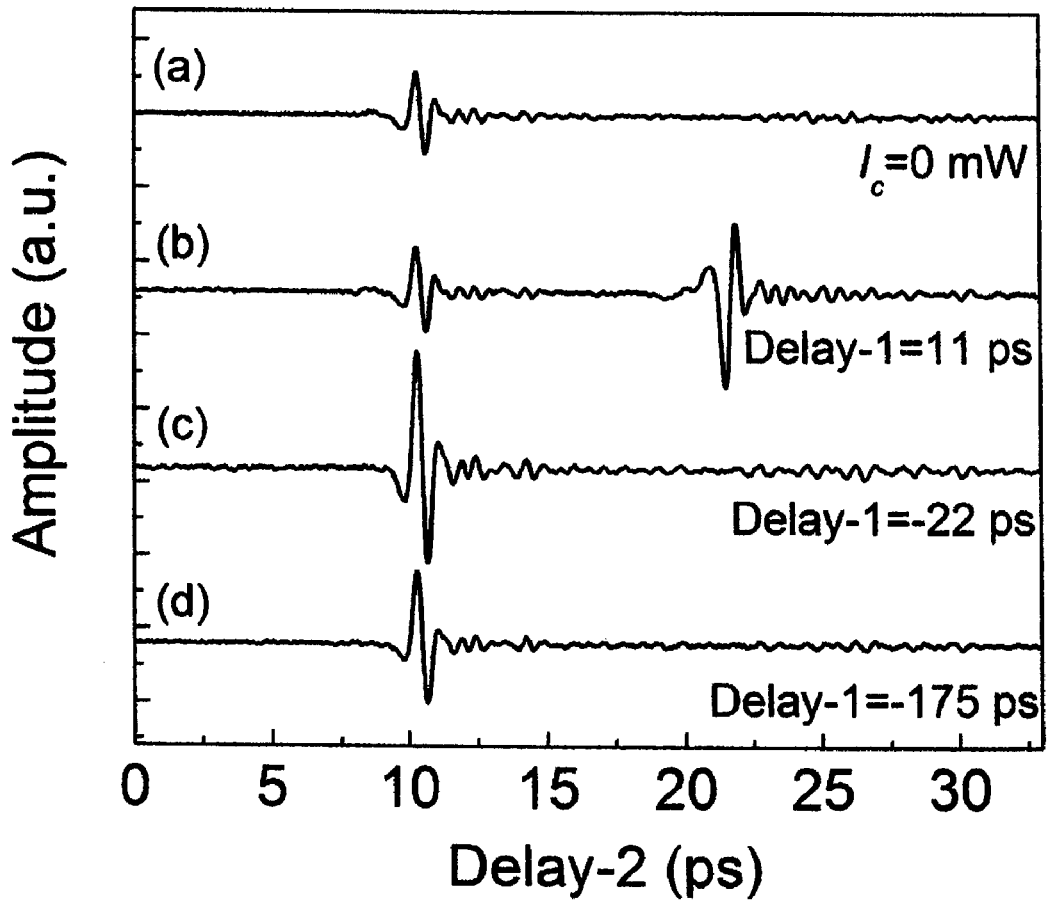
FIG. 2 are plots of the terahertz temporal waveforms generated by an optical signal pulse and enhanced by the optical control pulse with different time delays between the optical control beam and the optical signal beam using the experimental setup of FIG. 1.

FIG. 2 are plots of the terahertz temporal waveforms generated by an optical signal pulse and enhanced by the optical control pulse with different time delays between the optical control beam and the optical signal beam using the experimental setup of FIG. 1. Both the optical control beam and the optical signal beam are p-polarized. In plot (a), the optical control beam is blocked and the optical signal beam has 160 µJ pulse energy. For the plots (b), (c) and (d), both the optical signal beam and the optical control beam have 160 µJ pulse energy. In plot (b), the optical control pulse is 11 ps after the optical signal pulse. In plot (c) and (d), the optical control beam is 22 ps and 175 ps, respectively, before the optical signal beam. The negative timing of Delay-1, plots (c) and (d), means that the optical control pulse leads the optical signal pulse. Therefore, the optical control pulse creates the first plasma (pre-ionization), the optical signal pulse generates the terahertz wave on the pre-ionization background.

Comparing plots (a) and (c), an enhanced factor of about 2.5 (i.e., 250%) of the terahertz wave is shown when the optical control beam leads the optical signal beam by 22 ps. This enhancement is not due to the constructive interference of the terahertz waves generated by the optical control beam and the optical signal beam. As shown by plot (d), when Delay-1 is at −175 ps, the interference between the two optical pulses and the interference between the two terahertz pulses generated by the two optical pulses are both negligible. The observed terahertz waveform is still enhanced compared to the case of plot (a) which is obtained in the absence of the optical control beam.

It is also noted, as shown by plot (b), that when the optical control beam arrives after the optical signal beam, two terahertz temporal waveforms are observed although only the optical signal beam is modulated and their separation is just Delay-1. The phases of the first and second waveform are different. In this case, when the optical signal beam arrives earlier, the plasma created by the optical signal beam acts as the ionized background and enhances the terahertz wave generated by the optical control beam. The second observed waveform may be understood as the pure enhancement. Considering the lock-in amplifier is set at the phase of the mechanical chopper modulating the optical signal beam, while the enhancement of the terahertz wave generated by the optical control beam is modulated by the optical signal beam induced plasma, these two waveforms have different phase.

Figure 3:
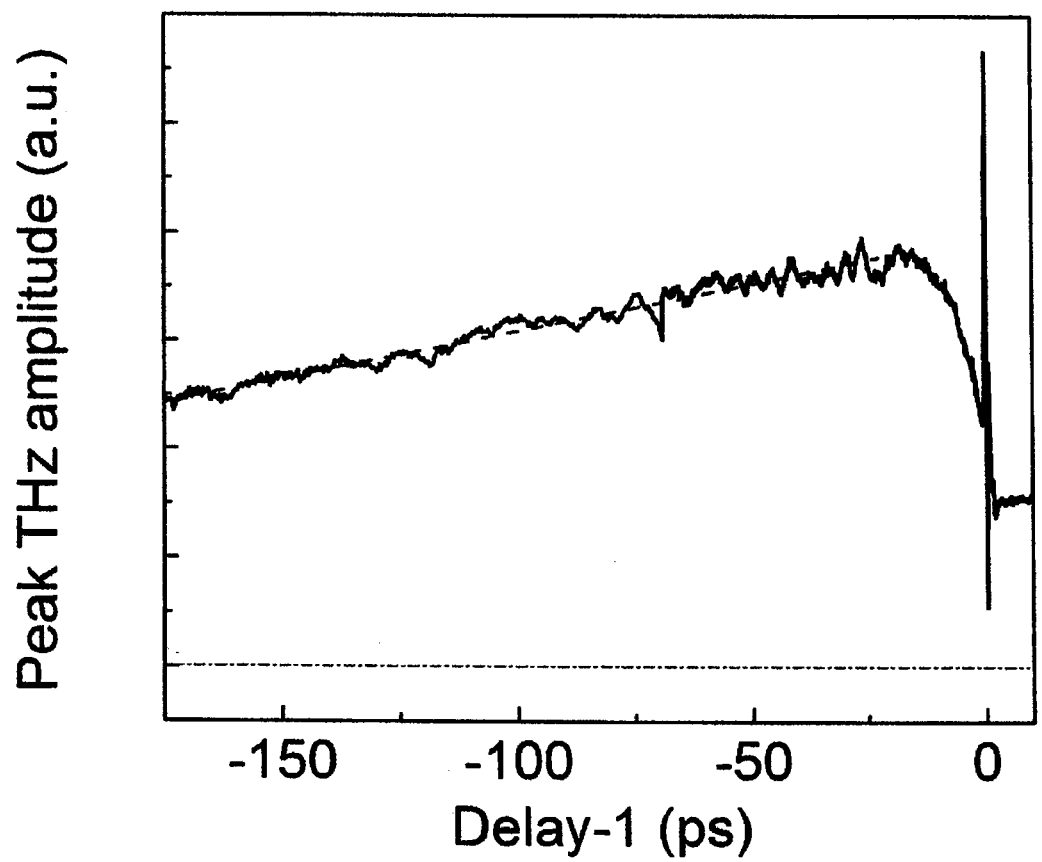
FIG. 3 is an enhancement as a function of the relative timing between the optical control pulse and the optical signal pulse using the experimental setup of FIG. 1.

The mechanism of terahertz wave generation from laser induced air plasma is the effect of ponderomotive force. When air is ionized by an intense laser beam, the difference in mass of the electrons and ions will cause a spatial separation of these opposite charges in the laser field. Thus, a net spatial dipole is formed and oscillates, which is the source of terahertz wave radiation. Therefore, if one laser beam ionizes air, other laser beams will benefit from the pre-created air plasma. Here we also attribute the enhancement phenomena to the ponderomotive force other than a third order nonlinear process due to the following reasons. First, other observed phenomena reveal enhanced $X^{(3)}$ in air plasma but this third order enhancement only happens in picosecond time scale and cannot explain the long time (102 ps) enhancement (as shown in FIG. 3). Second, it was also observed in the experiment that the enhancement is not sensitive to the optical control beam's polarization. When the polarization of the optical control beam was rotated, similar terahertz wave enhancement was also observed.

As a simple application, the enhancement was used to estimate the plasma lifetime. The method was to let Delay-1 stop where the amplitude of the terahertz waveform is at its maximum, and then scan Delay-2. As shown in FIG. 3, zero timing of Delay-1 means that the signal and control beams are temporally overlapped, and negative Delay-1 gives an earlier optical control beam. The dash-dot line in the figure gives the zero offset. Only in the initial several picoseconds after zero timing interference between the two terahertz waves is observed. Comparing to the peak terahertz amplitude at positive Delay-1, it is observed that enhancement lasts for over 175 ps. An exponential fit of 1/e gives 185 ps decay time as shown by the dashed curve. Under our experimental condition, carrier recombination should have a strong effect on plasma lifetime than that from the plasma diffusion in radical direction. By using parameters with estimated initial plasma density of $2\times10^{17}$ cm$^{-3}$ and plasma temperature 1 eV, the simulations shows about 200 ps plasma lifetime, this number agrees with the measured enhancement decay time of 185 ps.

Figure 4:
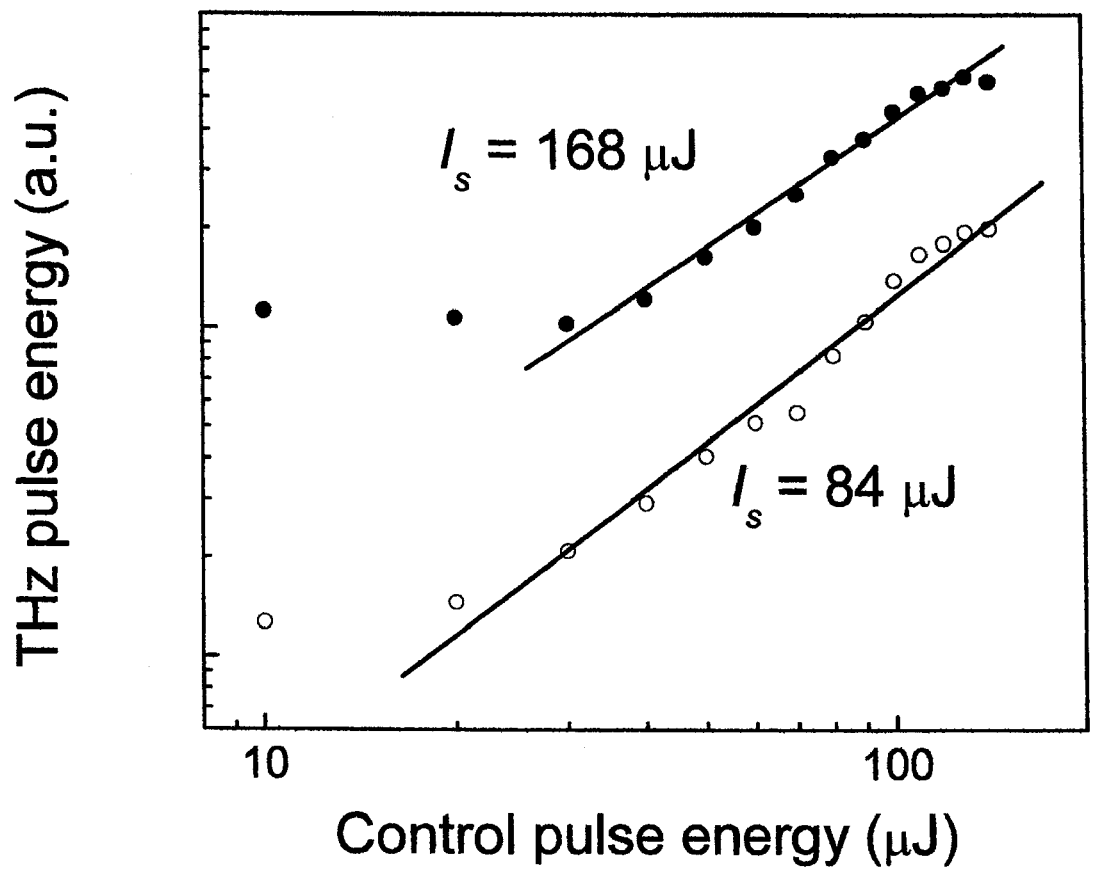
FIG. 4 is a plot of the power dependence of the enhancement on the optical control beam pulse energy using the experimental setup of FIG. 1.

FIG. 4 are plots of the power dependence of the terahertz energy enhancement on the optical control beam. Delay-1 is set at −22 ps and the optical signal pulse energy at 84 µJ and 168 µJ, respectively. At each optical control pulse energy level, a whole terahertz waveform is recorded by scanning the probe beam (Delay-2). Then, the integral over the square of the whole terahertz waveform gives the energy of the terahertz pulse.

As shown in FIG. 4, the enhancement shows the threshold behavior with an estimated value of 20 µJ corresponding to $10^{14}$ W/cm$^2$ intensity at the laser focus which is consistent with the previously reported air breakdown threshold. This observation provides further evidence to support plasma enhancing terahertz wave generation. Furthermore, when increasing the optical control pulse energy, enhanced terahertz pulse energy does not increase linearly. The two solid curves in the figure are the power fit of 1.2 (with $I_s$=168 µJ) and 1.4 (with $I_s$=84 µJ) obtained from a least-square fit. The enhancement is the benefit from the pre-ionized air plasma. When the optical signal beam arrives at the ionized background created by the optical control beam and excites all dipoles in its beam path, radiation from each dipole will coherently add up. Quantitive analysis is possible if the number of ions in the background plasma can be measured and relationship between it and the enhancement can be studied.

Thus, with ambient air as the medium, the enhancement of terahertz wave generation is demonstrated through pre-ionized air plasma. The amplitude of enhancement increases following the power law of the optical control laser beam intensity. And the enhancement lasting up to 175 ps is observed. It is possible to enhance a terahertz wave generation by using plasma created by gas discharge and laser ablation. By measuring the dependence of terahertz wave enhancement on plasma density and temperature, it is possible to optimized conditions for the enhancement and this also can be a promising tool for plasma diagnosis.

Figure 5A:
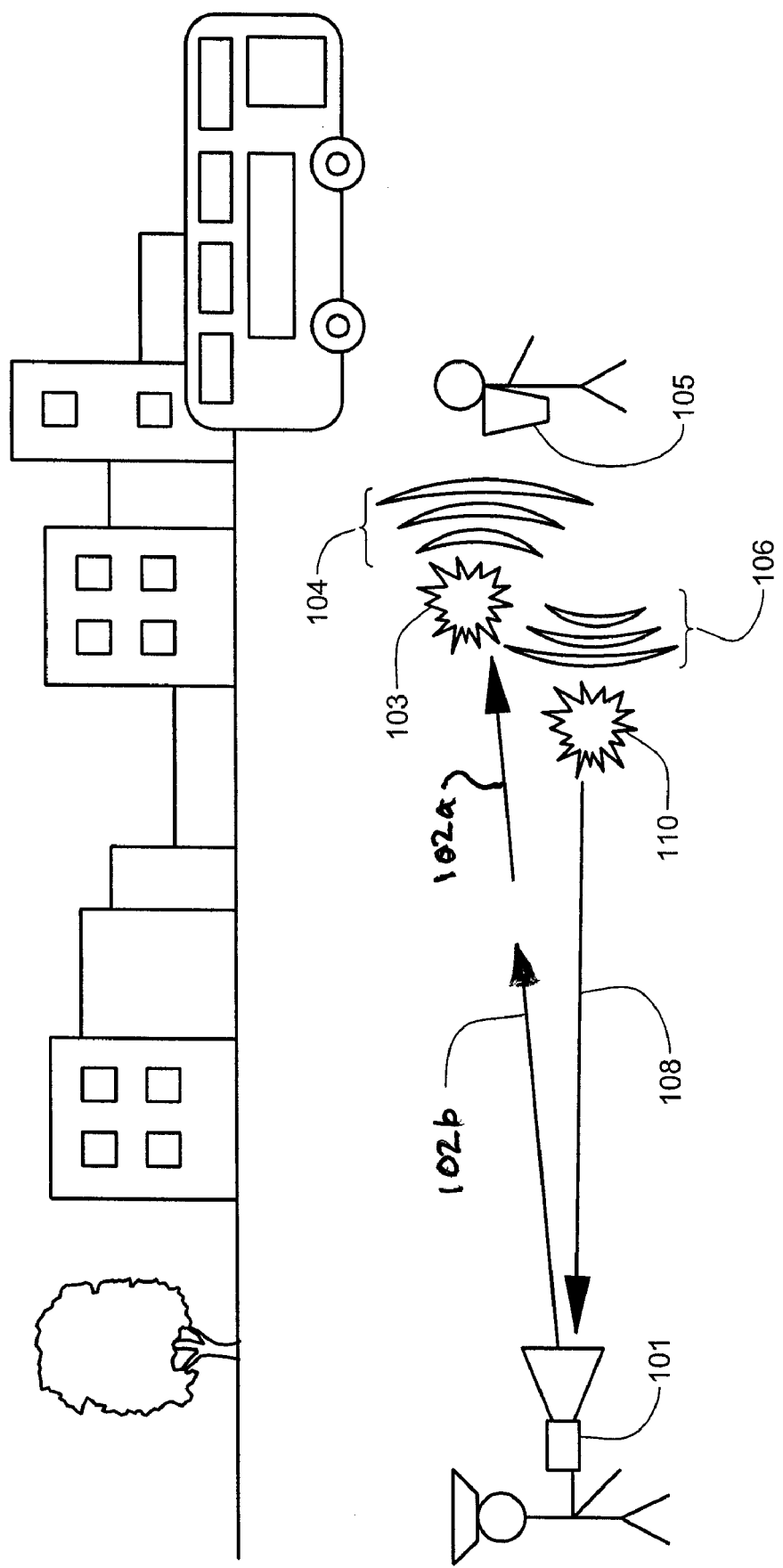
FIG. 5A illustrates one embodiment of a system for remotely analyzing an object in accordance with the present invention, wherein enhanced terahertz waves reflected by an object are detected.
Figure 5B:
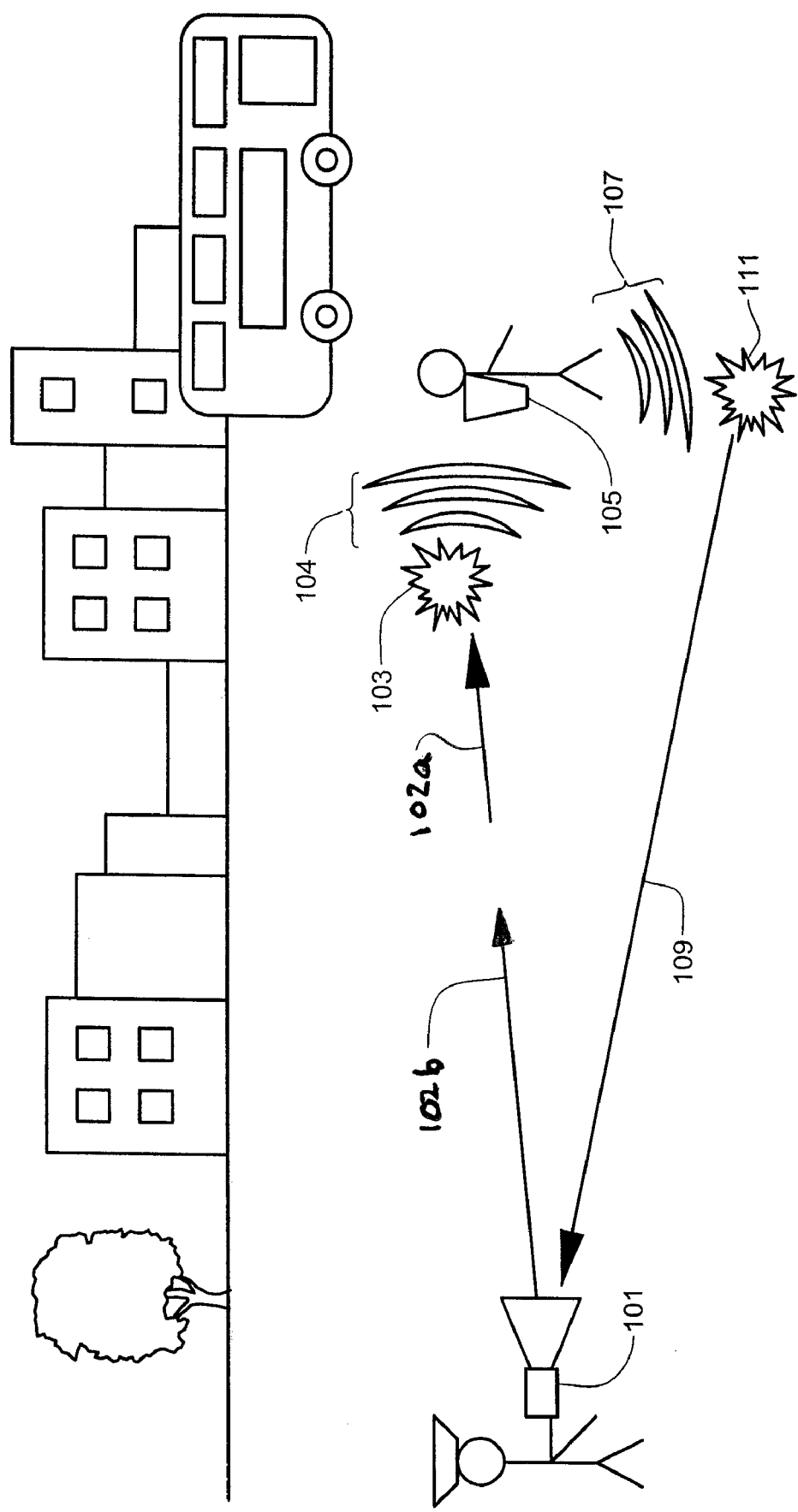
FIG. 5B illustrates one embodiment of a system for remotely analyzing an object in accordance with the present invention, wherein enhanced terahertz waves scattered by an object are detected.

Turning now to FIGS. 5A and 5B, therein illustrated is one embodiment of a system 101 for remotely analyzing an object 105 in an exemplary environment in which the system may be used. In this embodiment, an operator directs a first optical beam 102a and a time-delayed or temporally separated second optical beam 102b, rather than a terahertz beam, toward a target. The target reflects a portion of an enhanced terahertz wave 104 emitted by plasma 103 near the object. In FIG. 5A, a terahertz wave 106 reflected by the object is sensed by sensor plasma 110 near the object. The sensor plasma 110 emits an optical wave 108, which carries the spectral signature of the object that was imposed on the reflected terahertz wave. In FIG. 5B, a terahertz wave 107 scattered by the object is sensed by sensor plasma 111 near the object. The sensor plasma 111 emits an optical wave 109, which carries the spectral signature of the object that was imposed on the scattered terahertz wave. The optical radiation emitted by the sensor plasma is detected by the remote analysis system which may be remotely located over 30 meters away from a laser source to sense the terahertz wave reflected or scattered by the object.

Figure 6A:
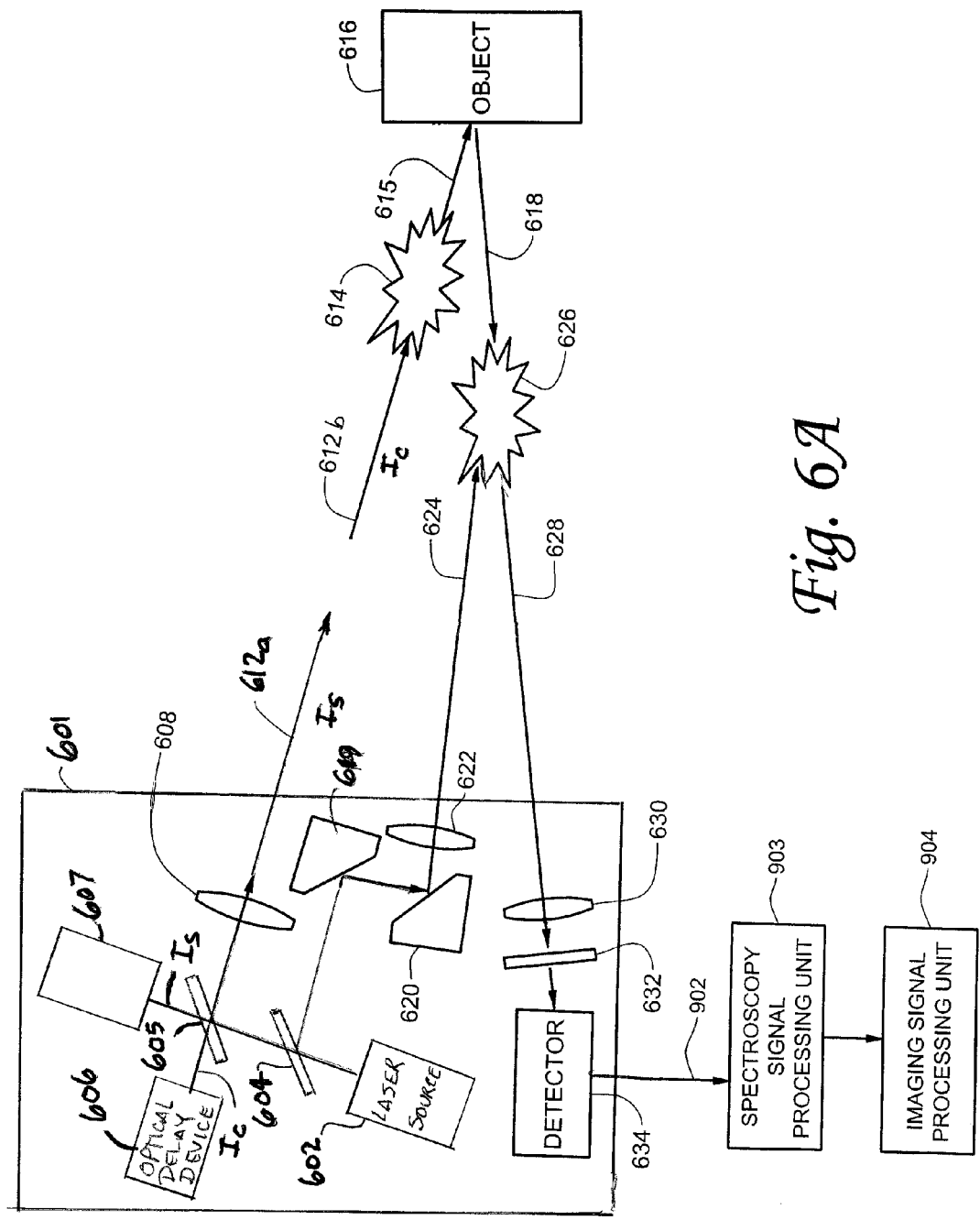
FIGS. 6A and 6B illustrate an embodiment of a system for analyzing a remotely-located object in accordance with the present invention.
Figure 6B:
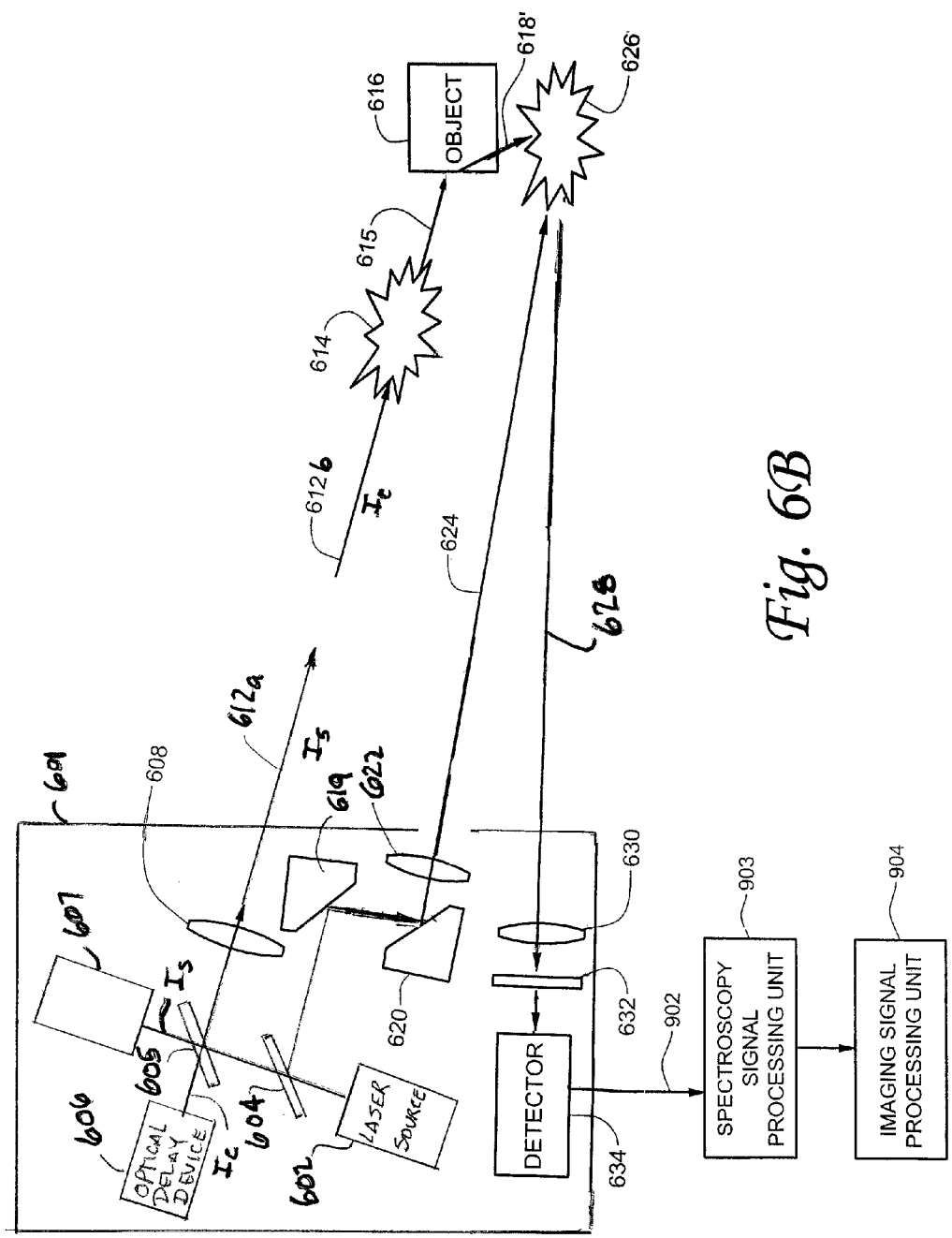

FIGS. 6A and 6B illustrate one embodiment of a system 601 for analyzing a remotely-located object, in accordance with another aspect of the present invention. This system comprises a source of an optical pump beam, means for splitting the optical pump beam into an optical control beam and an optical signal beam, means for focusing the optical control beam and the optical signal beam, a source of an optical probe beam, means for focusing an optical probe beam that is modulated with a signature of a targeted object that was imposed onto detected terahertz radiation by the object, and an optical detector. The optical control beam and the optical signal beam induce an ionized gas to generate enhanced terahertz radiation that is directed to an object to be analyzed. The terahertz radiation incident to the object interacts with the object, and the object reflects (as in FIG. 6A) or scatters (as in FIG. 6B) at least a portion of the incident terahertz radiation. A source of an optical probe beam provides a focused optical probe beam for ionizing a volume of ambient gas to produce a sensor plasma. The sensor plasma emits a resultant optical beam as a result of an interaction of the optical probe beam and the terahertz radiation reflected or scattered by the object. The resultant optical beam emitted by the sensor plasma is detected by an optical detector such as a photomultiplier tube, a photodiode, or other suitable detector.

In the embodiment of FIGS. 6A and 6B, the source of an optical pump beam comprises laser source 602, a first beamsplitter 604, a second beam splitter 605, optical delay device 606, a reflector 607, and lens 608. One example of optical delay device 606 comprises a series of mirrors arranged to increase the length of the optical radiation's propagation path of an optical control beam ($I_c$). Lens 608 focuses the optical beams provided by the laser source to produce a focused optical control beam 612a and a time-delayed focused optical signal beam 612b. In this embodiment, optical control beam and time-delayed optical signal beam ionizes the ambient gas in a volume to produce an emitter plasma 614. The interaction of optical control beam and optical signal beam with emitter plasma 614 induces the emitter plasma to emit enhanced terahertz radiation 615, as described above, propagating toward an object to be analyzed 616. In response to the incident terahertz radiation, the object reflects (as in FIG. 6A) or scatters (as in FIG. 6B) a portion of the incident terahertz radiation to produce reflected terahertz radiation 618 or scattered terahertz radiation 618'.

The system of FIGS. 6A and 6B also provides an optical probe beam 624, which ionizes the ambient gas in a volume to produce sensor plasma 626. Optical probe beam 624 is produced by beamsplitter 604, fixed mirror 619, adjustable mirror 620, and lens 622. Beamsplitter 604 directs a portion of the optical radiation from laser source 602 to mirror 619. Mirror 619 directs incident optical radiation from the beamsplitter to mirror 620 which directs the incident optical radiation to lens 622, which focuses the optical radiation from mirror 620 to provide optical probe beam 624. As a result of the interaction of optical probe beam 624 and reflected or scattered terahertz radiation 618 in sensor plasma 626, a resultant optical radiation 628 is emitted from the sensor plasma.

Resultant optical radiation 628, comprising, for example, a second harmonic frequency of the optical probe beam's fundamental frequency, is collimated by lens 630 and filtered by filter 632 to attenuate background optical radiation. Optical detector 634 detects a second harmonic component of resultant optical radiation 628 that is passed by filter 632. Optical detector 634 may comprise a photomultiplier detector, for example, or a photodiode, as another example.

The detected optical component may be analyzed. For example, system 601 additionally may include imaging signal processing unit 904, which is coupled to spectroscopy signal processing unit 903 for processing signal 902 which is provided by optical detector 634 in response to the detected component of resultant optical radiation 628. Imaging signal processing unit 904 produces a spectroscopic image of the targeted object, or a feature thereof, from an output of spectroscopy signal processing unit 903. Spectroscopy signal processing unit 903 and imaging signal processing unit 904 may comprise programs of instructions that are executable on a computer, microprocessor, or digital signal processor (DSP) chip, for example.

Figure 7A:
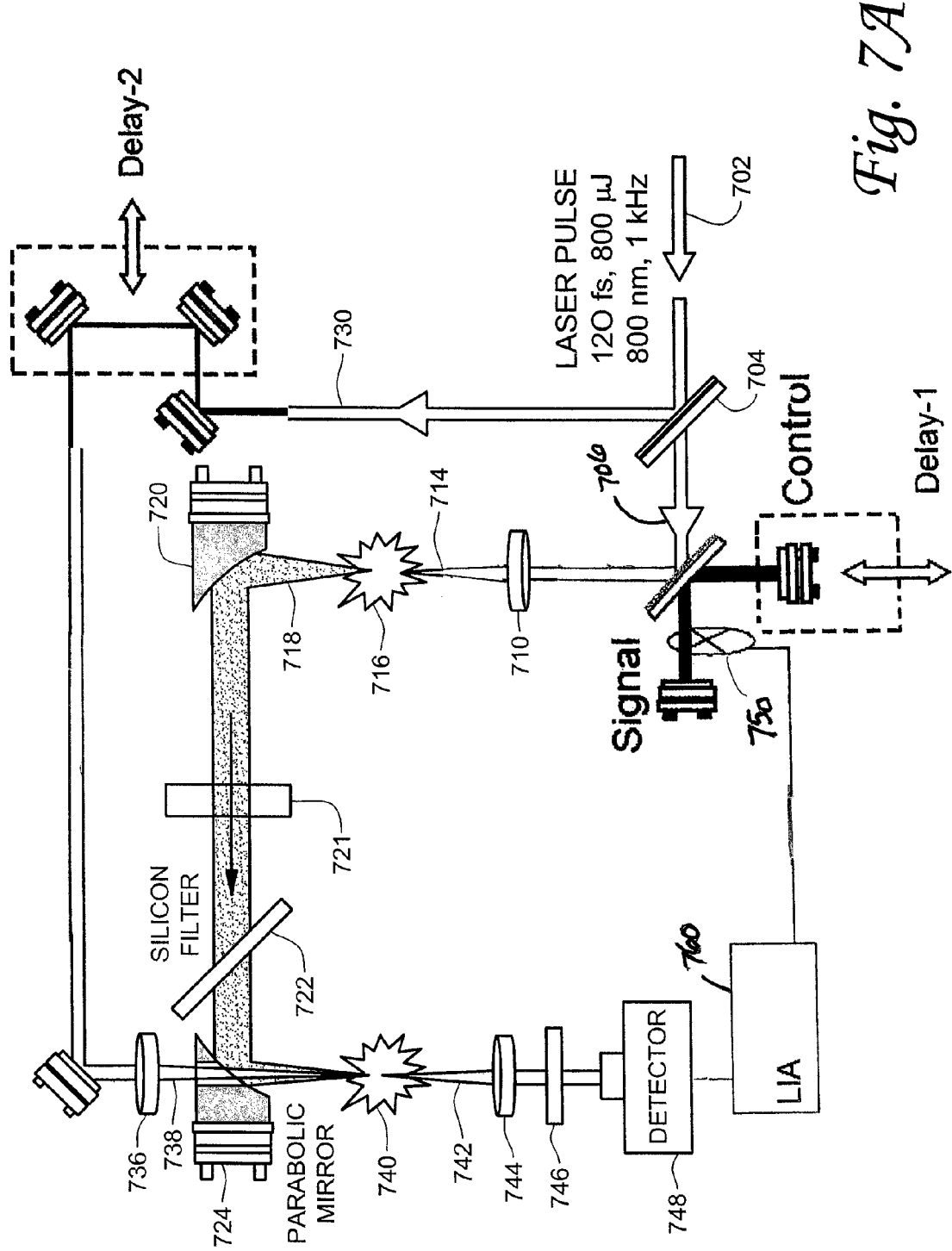
FIG. 7A illustrates an embodiment of a system that utilizes optically-induced ionized gas to emit and detect terahertz radiation to analyze objects, in accordance with the present invention, wherein a terahertz wave transmitted through a targeted object is detected.
Figure 7B:
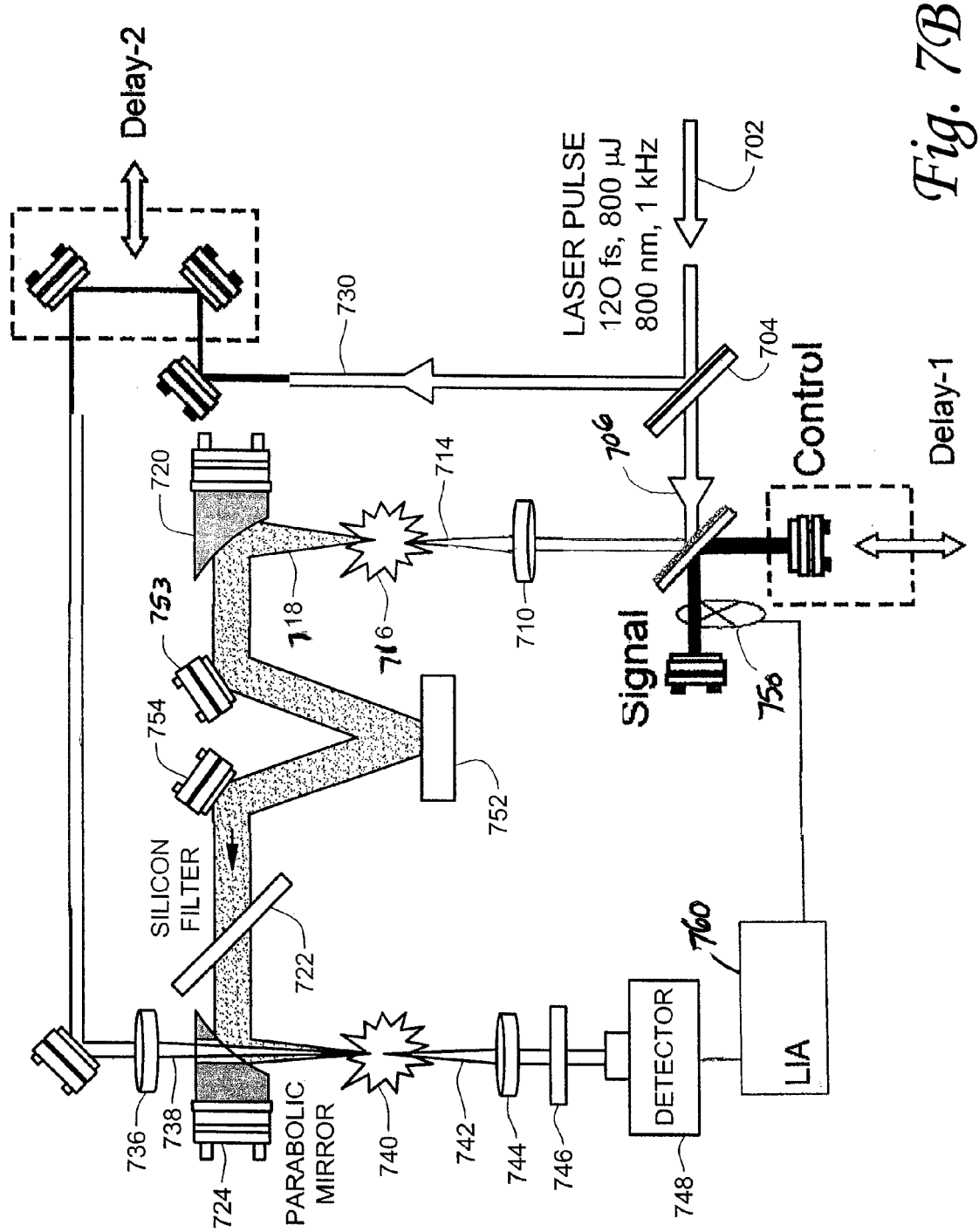
FIG. 7B illustrates an embodiment of a system that utilizes optically-induced ionized gas to emit and detect terahertz radiation to analyze objects in accordance with the present invention, wherein a terahertz wave reflected by a targeted object is detected.

FIGS. 7A and 7B illustrate embodiments of a system that utilizes optically-induced ionized gas to emit and detect terahertz radiation, in accordance with an aspect of the present invention. In FIG. 7A, a terahertz wave transmitted through the targeted object is measured, and, in FIG. 7B, a terahertz wave reflected by the object is measured.

A laser source such as a Ti: sapphire amplifier generates laser beam 702 comprising optical pulses. For example, the Ti: sapphire amplifier may generate 120 fs optical pulses at a repetition rate of 1 kHz with a central wavelength at 800 nm. In one example of this embodiment, the optical pulses of laser beam 702 have energies of 800 μJ or more. Laser beam 702 is split into two beams by a beamsplitter 704. One beam, fundamental pump beam 706, is used to generate terahertz waves, and the other beam, an optical probe beam 730, is used to detect the terahertz waves.

Fundamental pump beam 706 is also split by a 50/50 beam splitter to form a Michelson interferometer. One beam is an optical control beam ($I_c$), and the other beam is an optical signal beam ($I_s$). The time delay between the control beam and signal beam is scanned by a temporal delay stage (Delay-1), and a mechanical chopper 750 connected with a lock-in amplifier 760 placed in the optical signal beam path. The control and signal beams are then focused at the same point by a convex lens 710.

The optical control beam and the optical signal beam are focused in an ambient gas (for example, air) to produce emitter plasma 716 which emits an enhanced, as described in greater detail below, intense, highly directional, broadband terahertz wave 718.

In FIG. 7A, enhanced terahertz wave 718 is collimated by a parabolic mirror 720, transmitted through targeted object 721, and focused by refocusing mirror 724. In one embodiment, collimating mirror 720 may have a 76.2-mm diameter with a 101.6-mm effective focal length, and refocusing mirror 724 may have a 50.8-mm diameter and a 50.8-mm focal length. In FIG. 7B terahertz wave 718 is collimated by a parabolic mirror 720 and directed by metal mirrors 753 and 754, and targeted object 752 reflects the terahertz wave. In both embodiments, the terahertz wave is focused by a second parabolic mirror, refocusing mirror 724. Refocusing mirror 724 has a hole to allow focused probe beam 738 to pass through. Filter 722 transmits terahertz wave 718 and blocks the residual 800 nm and 400 nm beams. For example, filter 722 may comprise a high-resistivity silicon wafer.

Lens 736 focuses the probe beam in a volume of an ambient gas in which sensor plasma 740 is produced. Terahertz wave 718 is detected by the reciprocal process of its generation in which a second harmonic optical signal 742 is produced by mixing focused probe beam 738 and the incident terahertz field. A time-resolved measurement of second harmonic optical signal 742 provides coherent detection of the amplitude and phase of terahertz field 718.

In examples of the embodiments illustrated in FIGS. 7A and 7B, the terahertz wave and the probe beam are focused at the same point in sensor plasma 740. The terahertz-field-induced second harmonic optical signal is detected by a photo detector 748, e.g., a photomultiplier tube, a photodiode, or other suitable detector. Optionally, detection of second harmonic optical signal 742 may be improved by collimating the second harmonic optical signal with lens 744 and employing filter 746 to attenuate background optical radiation, including radiation at the optical probe beam's fundamental frequency. In the embodiments of FIGS. 7A and 7B, a unipolar waveform was detected when the probe beam intensity was less than about $1.8 \times 10^{14}$ W/cm$^2$, which is roughly the plasma threshold in air. Above this intensity level, the detected waveform begins to change, and above approximately $5.5 \times 10^{14}$ W/cm$^2$ the measured second harmonic waveform is bipolar and coherent detection is obtained.

The detected optical component may be analyzed and processed in a similar manner as discussed above.

Although various embodiments have been depicted and described in detail herein, it will be apparent to those skilled in the relevant art that modifications, additions, substitutions and the like can be made without departing from the spirit of the present invention and these are, therefore, considered to be within the scope of the present invention as defined in the following claims.

The invention claimed is:

1. A method for enhancing terahertz wave generation, the method comprising:
   providing a background plasma by directing a first optical beam in a volume of a gas; and
   enhancing pulsed terahertz wave generation by focusing a second time-delayed optical beam in the background plasma, the enhancement being an increased amplitude of the pulsed terahertz wave.

2. The method of claim 1 further comprising adjusting the time delay between the first optical beam and the second time-delayed optical beam.

3. The method of claim 1 further comprising optimizing the enhanced pulsed terahertz wave generation by adjusting the time delay between the first optical beam and the second time-delayed optical beam.

4. The method of claim 1 further comprising providing at least one pulse of optical radiation, and splitting the at least one pulse of optical radiation into the first optical beam and the second time-delayed optical beam.

5. The method of claim 1 further comprising turning on and off the second time-delayed optical beam in the background plasma.

6. The method of claim 1 wherein the providing comprises providing the background plasma near a targeted object, and the enhancing comprises enhancing pulsed terahertz wave generation directed toward the targeted object.

7. The method of claim 1 further comprising providing at a first location at least one source for the first optical beam and the second time-delayed optical beam, and wherein the providing the background plasma comprises providing the background plasma located more than 30 meters away from the first location.

8. The method of claim 1 wherein the providing comprises providing the background plasma near a targeted object comprising at least one of an explosive material, a biological agent, and a chemical agent, and the enhancing comprises enhancing pulsed terahertz wave generation directed toward the at least one of the explosive material, the biological agent, and the chemical agent.

9. The method of claim 1 wherein the time delay between the first optical beam and the second time-delayed optical beam is in the order of picoseconds.

10. The method of claim 1 wherein the time delay between the first optical beam and the second time-delayed optical beam is about 22 picoseconds.

11. A system for enhancing terahertz wave generation, said system comprising:
    a source for a first optical beam;
    means for directing the first optical beam to produce a background plasma in a volume of a gas;
    a source for a second time-delayed optical beam; and
    means for directing the second time-delayed optical beam in the background plasma to enhance pulsed terahertz wave generation, and
    wherein the enhancement being an increased amplitude in the pulsed terahertz wave.

12. The system of claim 11 further comprising means for adjusting the time delay between the first optical beam and the second time-delayed optical beam.

13. The system of claim 11 further comprising means for adjusting the time delay between the first optical beam and the second time-delayed optical beam to optimize the enhanced pulsed terahertz wave generation.

14. The system of claim 11 further comprising a source for providing an optical pump beam and means for splitting the optical pump beam to provide the first optical beam and the second time-delayed optical beam.

15. The system of claim 11 further comprising means for turning on and off the second time delayed optical beam in the background plasma.

16. The system of claim 11 wherein said means for directing the first optical beam comprises means for directing the first optical beam to produce the background plasma near a targeted object, and said means for directing the second time-delayed optical beam comprises means for directing the second time-delayed optical beam in the background plasma to enhance pulsed terahertz wave generation directed towards the targeted object.

17. The system of claim 11 wherein said first source and said second source are located at a first location, and said means for directing the first optical beam comprises means for directing the first optical beam to produce the background plasma in the volume of the ambient gas at a second location more than 30 meters away from the first location.

18. The system of claim 11 wherein the time delay between the first optical beam and the second time-delayed optical beam is in the order of picoseconds.

19. The system of claim 11 wherein the time delay between the first optical beam and the second time-delayed optical beam is about 22 picoseconds.

20. A method for detecting a remotely-located object, the method comprising:
    providing a background plasma by directing an optical control beam in a volume of a gas;

enhancing pulsed terahertz wave generation by directing a second time-delayed optical beam in the background plasma;

providing a sensor plasma by directing an optical probe beam in another volume of the gas; and detecting an optical component of resultant radiation produced from an interaction of the optical probe beam and an incident terahertz wave in the sensor plasma, the incident terahertz wave being produced by an interaction of the enhanced pulsed terahertz wave with the targeted object.

21. The method of claim 20 further comprising adjusting the time delay between the optical control beam and the time-delayed optical signal beam.

22. The method of claim 20 further comprising optimizing the enhanced pulsed terahertz wave generation by adjusting the time delay between the optical control beam and the time-delayed optical signal beam.

23. The method of claim 20 further comprising providing at least one pulse of optical radiation, and splitting the at least one pulse of optical radiation into the optical control beam, the time-delayed optical signal beam, and the optical probe beam.

24. The method of claim 20 further comprising turning on and off the time-delayed optical signal beam in the background plasma.

25. The method of claim 20 further comprising providing at a first location at least one source for the first optical beam and the second optical beam, and wherein the providing a background plasma comprises providing the background plasma located more than 30 meters away from the first location.

26. The method of claim 20 further comprising providing at a first location at least one source for the optical probe beam, and wherein the providing the sensor plasma comprises providing the sensor plasma more than 30 meters away from the first location.

27. The method of claim 20 further comprising analyzing the optical component of resultant radiation to detect at least one of an explosive material, a biological agent, and a chemical agent.

28. The method of claim 20 further comprising processing the optical component of resultant radiation to produce spectroscopy analysis data, and processing the spectroscopy analysis data to detect whether the target object comprises at least one of an explosive material, a biological agent, and a chemical agent.

29. The method of claim 20 wherein the time delay between the first optical beam and the second time-delayed optical beam is in the order of picoseconds.

30. The method of claim 20 wherein the time delay between the first optical beam and the second time-delayed optical beam is about 22 picoseconds.

31. The method of claim 20 wherein the detecting comprises detecting a terahertz waveform.

32. A system for detecting a remotely-located object, said system comprising:

a source for an optical control beam;

means for directing the optical control beam to produce a background plasma in a volume of a gas;

a source for a time-delayed optical signal beam;

means for directing the time-delayed optical signal beam in the background plasma to enhance pulsed terahertz wave generation directed towards the targeted object;

a source of an optical probe beam;

means for directing the optical probe beam to produce a sensor plasma in another volume of the gas; and an optical detector for detecting an optical component of resultant radiation emitted from the sensor plasma as a result of an interaction, in the sensor plasma, of the optical probe beam and a resultant terahertz wave, the resultant terahertz wave comprising terahertz radiation reflected, scattered, or transmitted by the targeted object in response to an interaction of the enhanced pulsed terahertz radiation with the targeted object.

33. The system of claim 32 further comprising means for adjusting the time delay between the optical control beam and the time-delayed optical signal beam.

34. The system of claim 32 further comprising means for adjusting the time delay between the optical control beam and the time-delayed optical signal beam to optimize the enhanced pulsed terahertz wave generation directed towards the targeted object.

35. The system of claim 32 further comprising a source for providing an optical pump beam, and means for splitting the optical pump beam to provide the optical control beam, the time-delayed optical signal beam, and the optical probe beam.

36. The system of claim 32 further comprising means for turning on and off the time-delayed optical signal beam.

37. The system of claim 32 wherein said means for directing the optical control beam is operable to produce the background plasma more than 30 meters away from said source for the optical control beam.

38. The system of claim 32 wherein said means for directing the optical probe beam is operable to produce the sensor plasma more than 30 meters away from said source for the optical probe beam.

39. The system of claim 32 further comprising means for analyzing the optical component of resultant radiation to detect at least one of an explosive material, a biological agent, and a chemical agent.

40. The system of claim 32 further comprising means for processing the optical component of resultant radiation to produce spectroscopy analysis data, and processing the spectroscopy analysis data to detect whether the target object comprises at least one of an explosive material, a biological agent, and a chemical agent.

41. The system of claim 32 wherein the time delay between the optical control beam and the time-delayed optical beam is in the order of picoseconds.

42. The system of claim 32 wherein the time delay between the optical control beam and the time-delayed optical beam is about 22 picoseconds.

43. The system of claim 32 wherein said optical detector for detecting the optical component comprises said optical detector for detecting a terahertz waveform.

* * * * *